United States Patent [19] [11] 4,113,882
Okazaki et al. [45] * Sep. 12, 1978

[54] STABILIZED ORAL PROSTAGLANDIN FORMULATION AND THE PROCESS FOR THE PREPARATION THEREOF

[75] Inventors: Kiyoshi Okazaki, Kawagoe; Masuo Murakami, Tokyo; Hiroitsu Kawada, Kawagoe; Jun Sekino, Kashiwa; Hidemi Shimizu, Tokyo; Shigemi Kawahara, Higashikurume, all of Japan

[73] Assignee: Yamanouchi Pharmaceutical Co., Ltd., Tokyo, Japan

[*] Notice: The portion of the term of this patent subsequent to Jul. 19, 1994, has been disclaimed.

[21] Appl. No.: 686,154

[22] Filed: May 13, 1976

Related U.S. Application Data

[63] Continuation-in-part of Ser. No. 516,217, Oct. 21, 1974, Pat. No. 4,036,954.

[30] Foreign Application Priority Data

May 20, 1975 [JP] Japan .................................. 50/60070

[51] Int. Cl.² ..................... A61K 31/19; A61K 31/215
[52] U.S. Cl. ..................................... 424/317; 424/305
[58] Field of Search ................................ 424/305, 317

[56] References Cited

U.S. PATENT DOCUMENTS 3,952,004  4/1976  Monkhouse .......................... 424/317

*Primary Examiner*—Sam Rosen
*Attorney, Agent, or Firm*—Burgess, Ryan and Wayne

[57] ABSTRACT

There is disclosed a dry, stabilized oral pharmaceutical formulation containing a prostaglandin E group prepared from a lyophilized composition comprising a prostaglandin E group and at least a member selected from the group consisting of a thiol compound, dextrin, dextran, a lower alkyl cellulose, and a water-soluble salt of deoxycholic acid.

18 Claims, No Drawings

STABILIZED ORAL PROSTAGLANDIN FORMULATION AND THE PROCESS FOR THE PREPARATION THEREOF

CROSS REFERENCE TO RELATED APPLICATION

This application is a continuation-in-part of our co-pending application Ser. No. 516,217, filed Oct. 21, 1974 now U.S. Pat. No. 4,036,954.

BACKGROUND OF THE INVENTION

1. Field of the Invention

The present invention relates to a stabilized oral pharmaceutical formulation of prostaglandin E group (hereinafter, it is referred to as PGE group) and a process of preparing the formulation. More particularly, the invention relates to a stabilized oral PGE group formulation prepared from the lyophilized composition of an aqueous solution containing PGE group and at least a member selected from the group consisting of a thiol compound, dextrin, dextran, a lower alkyl cellulose, and a water-soluble salt of deoxycholic acid and a process of preparing the formulation.

2. Description of the Prior Art

PGE is the compound shown by the following formula

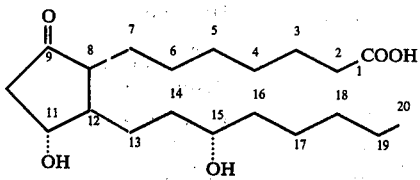

The compounds having the above-described basic structure include as $PGE_1$, $PGE_2$, $PGE_3$, etc., and they are named according to the number of the double bonds in the structure. For example, $PGE_2$ has two double bonds at the 5-position and 13-position of the structure. The PGE group in this invention includes the compounds having substituents such as the methyl group, methoxy group hydroxy group, oxo group, etc., at various positions of the structure. Typical examples of the $PGE_2$ group are, for example, 16-methyl-$PGE_2$, 3-methyl-$PGE_2$, 3,16(R)-dimethyl-$PGE_2$, 17-oxo-15-epi-$PGE_2$, 16(R)-hydroxy-$PGE_2$, 16,16-dimethyl-$PGE_2$-methyl ester, 4(R),16(R)-dimethyl-$PGE_2$, 4(R),16(S)-dimethyl-$PGE_2$, 4(S),16(R)-dimethyl-$PGE_2$, 4(S),16(S)-dimethyl-$PGE_2$, 16(R,S)-methyl-20-methoxy-$PGE_2$, 16(R)-methyl-20-methoxy-$PGE_2$, and 16(S)-methyl-20-methoxy-$PGE_2$.

The PGE group exhibits, even at a small dose, wide pharmaceutical effects such as control of the contractive force of the uterus or of hypotensitive activity, the treatment and prophylaxis of digestive organ ulcers, the control of lipid metabolism, bronchodilator activity, etc., but has a fault in that the aqueous solution thereof is unstable (see, Brummer, "J. Pharm. Pharmacol.", 23, 804–805(1971) and Karmin et al; "European J. Pharmacol.", 4, 416–420(1968).

For preparing stable compositions of $PGE_2$, there are known, for example, a method of preparing a concentrated stock solution of $PGE_2$ by dissolving it in absolute alcohol as disclosed in U.S. Pat. No. 3,749,800 and a method of preparing a solution of $PGE_2$ by dissolving it in an anhydrous aprotic dipolar organic solvent such as N,N-dimethylacetamide as disclosed in Belgian Pat. No. 790,840. When the compositions of $PGE_2$ prepared by these methods are used as injections, they are usually diluted with water.

There is also known a method of stabilizing the PGE group by adding thereto an alkali metal sulfite salt as disclosed in U.S. Pat. No. 3,851,052 but the case of showing practically the stabilization effect by the method is limited to a stock solution of PGE prepared by dissolving it in alcohol together with an alkali metal sulfite salt and even in this case, however the potency of the solution about the stability becomes only about 70% when the solution is stored for 13 days at 60° C.

Moreover, there is known a method of preparing a solid dispersion of prostaglandin in polyvinyl pyrrolidone as disclosed in U.S. Pat. No. 3,826,823. According to said method, 1 part of prostaglandin is dissolved in a suitable solvent together with 10–100 parts of polyvinyl pyrrolidone and then the solution is dried by, for example, lyophilization to disperse the prostaglandin in polyvinyl pyrrolidone. However, the method is accompanied by the disadvantage in that a small amount of water in the solution does not evaporate completely by lyophilization due to the high hygroscopicity of the polyvinyl pyrrolidone itself and also the lyophilized product obtained is liable to be decomposed by the remaining water. Therefore, the lyophilization procedure must be conducted for a long period of time. Still further, in the case of preparing formulations such as, for example, tablets using the lyophilized composition thus obtained, the composition becomes sticky by absorbing ambient moisture. This will clearly cause difficulties in preparing the composition. Further, the moisture way also causes the possibility of the decomposition of PEG group. These difficulties had not yet been solved.

SUMMARY OF THE INVENTION

As the result of various investigations to provide a stable oral formulation of PGE group, the inventors have discovered that the composition of the PGE group prepared by dissolving the PGE group in an aqueous solution of a thiol compound, dextrin, dextran, a lower alkylcellulose, or a water-soluble salt of deoxycholic acid and lyophilizing the solution is stable, the composition can maintain its stability sufficiently when an oral formulation is prepared from the lyophilized composition of the PGE group, and further the composition can maintain its stability after the preparation of the formulation.

DESCRIPTION OF THE PREFERRED EMBODIMENTS

As the thiol compound used in this invention, there are glutathione, cysteine, N-acetylcysteine etc. As the lower alkylcellulose used in this invention, there are methylcellulose, ethylcellulose, etc. Also, as the water soluble salt of deoxycholic acid, there are alkali metal salts such as sodium salt, potassium salt, etc., and basic amino acid salts such as arginine salt, lysine salt, etc.

The lyophilized composition of the group PGE used in this invention can be prepared in the following manner. That is, the PGE group is usually dissolved in water together with the thiol compound, dextrin, dextran, the lower alkylcellulose, hydroxyethyl cellulose, hydroxypropyl cellulose, carboxymethyl cellulose, or the water soluble salt of deoxycholic acid and then after adjusting, if necessary, the property of the solution, the aqueous solution is lyophilized by an ordinary manner.

In this case, the thiol compound, dextrin, dextran, the lower alkylcellulose, and the water soluble salt of deoxycholic acid may be used individually or as a combination of any desired two or more components. Furthermore, in the case of using the water soluble salt of deoxycholic acid, deoxychloric acid may be dissolved beforehand in water together with an inorganic or organic base which will form the water soluble salt of deoxycholic acid.

In addition, the PGE group itself is soluble in water but requires
   a long period of time to be dissolved completely in water and hence it is advantageous that PGE group is transformed beforehand into an amorphous form to enlarge the contact area with water by dissolving the crystal of the PGE group in a small amount of a volatile solvent such as ethanol and ethyl acetate and then distilling off the solvent.

There is no particular limitation about the volume ratio of PGE group and the additive such as the thiol compound, dextrin, dextran, the lower alkylcellulose, and the water soluble salt of deoxycholic acid but the proper ratio is 1–20 mg. for the thiol compound, 5–250 mg. for dextrin, dextran, or the lower alkylcellulose, or 5–100 mg. for the water soluble salt of deoxycholic acid, per 20–150γ of PGE group.

Since the lyophilized composition of PGE group thus obtained has a very high stability, it can be stored without
   decomposition until the composition is used for preparing the formulation. Moreover, the stability of the composition of PGE group is not reduced when subject to the operation in preparing oral formulations such as tablets, capsules, powders, granules, etc., from the composition.

At the preparation of the formulations, the lyophilized composition of PGE group thus obtained is powdered and then formed into tablets, capsules, granules, powders, etc., by an ordinary way together with carrier which is usually employed for preparing such formulations. Examples of suitable non-toxic solid carriers used for the purpose include, pharmaceutical grades of mannitol, lactose, starches, magnesium stearate, talcum, and the like.

EXAMPLES 1–13

In a two liter vessel was placed a solution of 50 mg. of each of the prostaglandin E groups shown in Table 2 in 1 ml. of ethanol and after wetting the wall of the vessel with the solution, ethanol was distilled off under reduced pressure or nitrogen gas stream. The additives shown in the following table and 1,500 ml. of distilled water were added to the residue to dissolve the additive and then the pH of the solution was adjusted to 6.5 by adding an aqueous sodium hydroxide solution with stirring to dissolve the prostaglandin E group. Thereafter, distilled water was added to the solution to make the total amount to 2,000 ml. and then the solution was lyophilized.

Table 1

| Example | Prostaglandin E group | Additive | Amount of additive |
|---|---|---|---|
| 1 | 4(R),16(R)-Dimethyl-PGE$_2$ (I) | Dextran 20* | 400 g. |
| 2 | (I) | Dextrin | 100 g. |
| 3 | 4(S),16(R)-Dimethyl-PGE$_2$(II) | Dextran 20* | 400 g. |
| 4 | (II) | Dextrin | 100 g. |
| 5 | 4(S),16(S)-Dimethyl-PGE$_2$(III) | Dextran 70** | 120 g. |

Table 1-continued

| Example | Prostaglandin E group | Additive | Amount of additive |
|---|---|---|---|
| 6 | (III) | Dextrin | 100 g. |
| 7 | 4(R),16(S)-Dimethyl-PGE$_2$ (IV) | Dextran 20* | 400 g. |
| 8 | (IV) | Dextrin | 100 g. |
| 9 | (IV) | Glutathione | 40 g. |
| 10 | 16(R,S)-Methyl-20-methoxy-PGE$_2$ (V) | Dextran 70** | 120 g. |
| 11 | (V) | Dextrin | 100 g. |
| 12 | (V) | Deoxycholic acid arginine salt | 60 g. |
| 13 | (V) | Glutathione | 40 g. |

(*):Mean molecular weight of 20,000
(**):Mean molecular weight of 70,000.

In addition, for determining the stabilities of the lyophilzed products obtained in Examples 1–13, 1 ml of each of the solutions of the prostaglandin E groups prepared in the examples was lyophilized separately, stored for 10 days at 50° C., the content of each prostaglandin E group was measured, and the remained percentage thereof was calculated. The results are shown in Table 2.

Table 2

| Example | Prostaglandin E group | Additive | Remained percentage |
|---|---|---|---|
| 1 | (I) | Dextran 20* | 79.0% |
| 2 | (I) | Dextrin | 88.8% |
| Control | (I) | none | 30.5% |
| 3 | (II) | Dextran 20* | 79.5% |
| 4 | (II) | Dextrin | 88.7% |
| Control | (II) | none | 29.6% |
| 5 | (III) | Dextran 70** | 83.7% |
| 6 | (III) | Dextrin | 83.6% |
| Control | (III) | none | 30.1% |
| 7 | (IV) | Dextran 20* | 78.6% |
| 8 | (IV) | Dextrin | 90.1% |
| 9 | (IV) | Glutathione | 85.9% |
| Control | (IV) | Mannitol | 20.6% |
| Control | (IV) | none | 31.9% |
| 10 | (V) | Dextran 70** | 83.3% |
| 11 | (V) | Dextrin | 94.5% |
| 12 | (V) | Deoxycholic acid arginine salt | 100.4% |
| 13 | (V) | Glutathione | 90.7% |
| Control | (V) | Mannitol | 26.9% |
| Control | (V) | none | 39.4% |

(*):Mean molecular weight of 20,000
(**):Mean molecular weight of 70,000.

EXAMPLE 14

In a two liter vessel was placed a solution of 50 mg. of 16(R,S)-methyl-20-methoxy-prostaglandin E$_2$ in 1 ml. of ethanol and after wetting the wall of the vessel with the solution, ethanol was distilled off under reduced pressure or nitrogen gas stream. Then, 10 g. of methylcellulose and 1,500 ml. of distilled water were added to the residue to dissolve methylcellulose and then the pH of the solution was adjusted to 6.5 by adding an aqueous sodium hydroxide solution with stirring to dissolve the 16(R,S)-methyl-20-methoxy-prostagrandin E$_2$. Thereafter, distilled water was added to make the total amount to 2,000 ml. and the solution was lyophilized.

One ml. of the solution of the prostaglandin E$_2$ prepared in the above example was lyophilized separately and stored for 10 days at 50° C. The percentage of 16(R,S)-methyl-20-methoxy-prostaglandin E$_2$ in the stored sample was 95.1%.

EXAMPLES 15–19

In a two liter vessel was placed a solution of 50 mg. of 16(S)-methyl-20-methoxy-prostaglandin E$_2$ (referred to as (VI)) in 1 ml. of ethanol and after wetting the wall of the vessel with the solution, ethanol was distilled off under a reduced pressure or nitrogen gas stream. Then, the additive shown in Table 5 and 1,500 ml. of distilled water to dissolve the additive were added and then the pH of the solution was adjusted to 6.5 by adding thereto an aqueous sodium hydroxide solution with stirring to dissolve the prostaglandin E group. Thereafter, distilled water was added to the solution to make the total amount to 2,000 ml.

The solution thus prepared was filtered, filled in a tray, and after lyophilizing the solution, the product was pulverized. The lyophilized composition thus obtained was allowed to stand for 10 days at 50° C. and thereafter the remained percentage of the prostaglandin E group was measured. The results are shown in the following table.

Table 3

| Ex. No. | Prostaglandin E group | Additive | Addition amount | Remained percentage |
|---|---|---|---|---|
| 15-a | 16(S)-Methyl-20-methoxy-PGE$_2$(VI) | Deoxycholic acid arginine salt | 60 g. | 99% |
| 16-a | (VI) | Dextran 70 | 120 g. | 85% |
| 17-a | (VI) | Glutathione | 40 g. | 93% |
| 18-a | (VI) | Dextrin | 100 g. | 92% |
| 19-a | (VI) | Hydroxypropyl methylcellulose | 20 g. | 84% |
| Control | (VI) | none | 0 | 38% |
| Control | (VI) | Mannitol | 111 g. | 25% |

Formulations having the compositions shown in Table 4 were prepared using the prostaglandin-containing powders (referred to as PG-powder) obtained in aforesaid Examples 15-a to 19-a and also the remained percentages of the prostaglandin E groups in the formulations were determined by the same manner as above. The results are shown in the following table.

TABLE 4

EXAMPLE 15-b-1

| Tablet | Amount in one tablet |
|---|---|
| PG-powder (prepared in Example 15-a) | 30 mg. |
| Crystalline cellulose | 120 mg. |
| Calcium hydrogenphosphate | 87 mg. |
| Carboxymethylcellulose calcium | 4 mg. |
| Light silicic anhydride | 1 mg. |
| Talc | 4 mg. |
| Magnesium stearate | 4 mg. |

The remaining percentage when stored for 10 days at 50° C. was 98%.

EXAMPLE 15-b-2

| Tablet | Amount in one tablet |
|---|---|
| PG-powder (prepared in Example 15-a) | 30 mg. |
| Crystalline cellulose | 151 mg. |
| Hydroxypropyl cellulose | 3 mg. |
| Starch | 10 mg. |
| Talc | 4 mg. |
| Magnesium stearate | 2 mg. |

The remaining percentage when stored for 10 days at 50° C. was 100%.

EXAMPLE 15-b-3

| Powder | |
|---|---|
| PG-powder (prepared in Example 15-a) | 30 mg. |
| Lactose | 250 mg. |
| Starch | 50 mg. |
| D-mannitol | 100 mg. |

The remaining percentage when stored for 10 days at 50° C. was 99%.

EXAMPLE 16-b-1

| Tablet | Amount in one tablet |
|---|---|
| PG-powder (prepared in Example 16-a) | 60 mg. |
| Crystalline cellulose | 90 mg. |
| Calcium hydrogenphosphate | 87 mg. |
| Carboxymethylcellulose sodium | 4 mg. |
| Light silicic anhydride | 1 mg. |
| Talc | 4 mg. |
| Magnesium stearate | 4 mg. |

The remaining percentage when stored for 10 days at 50° C. was 85%.

EXAMPLE 16-b-2

| Tablet | Amount in one tablet |
|---|---|
| PG-powder (prepared in Example 16-a) | 60 mg. |
| Crystalline cellulose | 121 mg. |
| Hydroxypropyl cellulose | 3 mg. |
| Carboxymethylcellulose calcium | 10 mg. |
| Talc | 4 mg. |
| Magnesium stearate | 2 mg. |

The remaining percentage when stored for 10 days at 50° C. was 86%.

EXAMPLE 16-b-3

| Tablet | Amount in one tablet |
|---|---|
| PG-powder (prepared in Example 16-a) | 60 mg. |
| Crystalline cellulose | 121 mg. |
| Hydroxypropyl cellulose | 3 mg. |
| Carboxymethylcellulose sodium | 10 mg. |
| Talc | 4 mg. |
| Magnesium stearate | 2 mg. |

The remaining percentage when stored for 10 days at 50° C. was 85%.

EXAMPLE 16-b-4

| Capsule | Amount in one capsule |
|---|---|
| PG-powder (prepared in Example 16-a) | 60 mg. |
| Lactose | 300 mg. |
| Starch | 85 mg. |
| D-mannitol | 2.5 mg. |
| Talc | 10 mg. |
| Magnesium stearate | 2.5 mg. |

The remaining percentage when stored for 10 days at 50° C. was 84%.

EXAMPLE 17-b

| Tablet | Amount in one tablet |
|---|---|
| PG-powder (prepared in Example 17-a) | 20 mg. |
| Crystalline cellulose | 130 mg. |
| Calcium hydrogenphosphate | 87 mg. |
| Carboxymethylcellulose calcium | 4 mg. |
| Light silicic anhydride | 1 mg. |

-continued

| Tablet | Amount in one tablet |
| --- | --- |
| Talc | 4 mg. |
| Magnesium stearate | 4 mg. |

The remaining percentage when stored for 10 days at 50° C. was 92%.

EXAMPLE 18-b-1

| Tablet | Amount in one tablet |
| --- | --- |
| PG-powder (prepared in Example 18-a) | 50 mg. |
| Crystalline cellulose | 100 mg. |
| Calcium hydrogenphosphate | 87 mg. |
| Carboxymethylcellulose calcium | 4 mg. |
| Light silicic anhydride | 1 mg. |
| Talc | 4 mg. |
| Magnesium stearate | 4 mg. |

The remaining percentage when stored for 10 days at 50° C. was 94%.

EXAMPLE 18-b-2

| Capsule | Amount in one capsule | |
| --- | --- | --- |
| PG-powder (prepared in Example 18-a) | 50 | mg. |
| Lactose | 300 | mg. |
| Starch | 85 | mg. |
| D-mannitol | 2.5 | mg. |
| Talc | 10 | mg. |
| Magnesium stearate | 2.5 | mg. |

The remaining percentage when stored for 10 days at 50° C. was 96%.

EXAMPLE 19-b-1

| Tablet | Amount in one tablet |
| --- | --- |
| PG-powder (prepared in Example 19-a) | 10 mg. |
| Crystalline cellulose | 140 mg. |
| Calcium hydrogenphosphate | 87 mg. |
| Carboxymethylcellulose sodium | 4 mg. |
| Light silicic anhydride | 1 mg. |
| Talc | 4 mg. |
| Magnesium stearate | 4 mg. |

The remaining percentage when stored for 10 days at 50° C. was 85%.

EXAMPLE 19-b-2

| Powder | |
| --- | --- |
| PG-powder (prepared in Example 19-a) | 10 mg. |
| Lactose | 250 mg. |
| Starch | 50 mg. |
| D-mannitol | 100 mg. |

The remaining percentage when stored for 10 days at 50° C. was 84%.

EXAMPLE 20

In a two liter vessel was placed a solution of 100 mg. of the crystals of 16-methyl-prostaglandin $E_2$ in 1 ml. of ethanol and after wetting the wall of the vessel with the solution, ethanol was distilled off from the solution under reduced pressure or nitrogen gas stream. Then, 400 g. of dextran 20 (mean molecular weight of 20,000) and 1500 ml. of distilled water were added to the residue to dissolve the solid components and after adding thereto distilled water to make the total amount thereof to 2,000 ml., the solution was lyophilized.

EXAMPLE 21

In a two liter vessel was placed a solution of 100 mg. of the crystal of 16-methyl-prostaglandin $E_2$ in 1 ml. of ethanol and after wetting the wall of the vessel with the solution, ethanol was distilled off from the solution under reduced pressure or nitrogen gas stream. Then, 120 g. of dextran 70 (mean molecular weight of 70,000) and 1,500 ml. of distilled water were added to the residue to dissolve the solid components and after adding thereto distilled water to make the total amount to 2,000 ml., the solution was lyophilized.

EXAMPLE 22

In two liter vessel was placed a solution of 100 mg. of the crystals of 3-methyl-prostaglandin $E_2$ in 1 ml. of ethanol and after wetting the wall of the vessel with the solution, ethanol was distilled off under reduced pressure or nitrogen gas stream. Then, 120 g. of dextran 20 (mean molecular weight of 20,000) and 1,500 ml. of distilled water were added to the residue to dissolve the solid components and after adding thereto distilled water to make the total amount to 2,000 ml., the solution was lyophilized.

EXAMPLE 23

In two liter vessel was placed a solution of 100 mg. of the crystal of 3,16(R)-dimethyl-prostaglandin $E_2$ in 1 ml. of ethanol and after wetting the wall of the vessel with the solution, ethanol was distilled off under reduced pressure or nitrogen gas stream. Then, 120 g. of dextran 20 (mean molecular weight of 20,000) and 1,500 ml. of distilled water were added to the residue to dissolve the solid components and after adding thereto distilled water to make the total amount to 2,000 ml., the solution was lyophilized.

EXAMPLE 24

In two liter vessel was placed a solution of 100 mg. of the crystals of 17-oxo-15-epi-prostaglandin $E_2$ in 1 ml. of ethanol and after wetting the wall of the vessel with the solution, ethanol was distilled off under reduced pressure or nitrogen gas stream. Then, 100 g. of dextrin and 1,500 ml. of distilled water were added to the residue to dissolve the dextrin and then the pH of the solution was adjusted to 6.5 by adding thereto an aqueous sodium hydroxide solution with stirring to dissolve 17-oxo-15-epi-prostaglandin $E_2$. Thereafter, distilled water was added to the solution to make the total amount to 2,000 ml. and the solution was lyophilized.

EXAMPLE 25

In two liter vessel was placed a solution of 100 mg. of the crystals of 16(R)-hydroxy-prostaglandin $E_2$ in 1 ml. of ethanol and after wetting the wall of the vessel with the solution, ethanol was distilled off under reduced pressure or nitrogen gas stream. Then, 40 g. of glutathione and 1,500 ml. of distilled water were added to the residue to dissolve the glutathione and the pH of the solution was adjusted to 6.5 by adding thereto an aqueous sodium hydroxide solution with stirring to dissolve 16(R)-hydroxy-prostaglandin $E_2$. Thereafter, distilled water was added to the solution to make the total amount to 2,000 ml. and the solution was lyophilized.

EXAMPLE 26

In two liter vessel was placed a solution of 100 mg. of the crystals of 16(R)-hydroxy-prostaglandin $E_2$ in 1 ml. of ethanol and after wetting the wall of the vessel with the solution, ethanol was distilled off under reduced pressure or Nitrogen gas stream. Then, 40 g. of oxidized type glutathione and 1,500 ml. of distilled water were added to the residue to dissolve the oxidized type glutathione and the pH of the solution was adjusted to 6.5 by adding an aqueous sodium hydroxide solution with stirring to dissolve 16(R)-hydroxy-prostaglandin $E_2$. Thereafter, distilled water was added to the solution to make the total amount to 2,000 ml. and the sloution was lyophilized.

The stabilities of the lyophilized compositions of PGE group prepared in reference Examples 1–7 are shown below.

Method of quantitative analysis of remaining PGE group each 1 ml. of 2000 ml. of each of the PGE group-containing aqueous solutions prepared in Reference Examples 1–7 was lyophilized separately in a vial for the analysis. It was dissolved in 1 ml. of water and after adjusting the pH thereof to 3 or below 3 by adding citric acid, the solution was extracted with ethyl acetate. The extract was dried and concentrated. Then, the total amount of the residue was subjected to a silica gel thin layer chromatography and developed by using a mixture of chloroform, methanol, acetic acid, and water (90 : 8 : 1 : 0.8 by volume ratio), after spraying an ethanol solution of 5% phosphorus molybdate over the developed product and heating to 105°–110° C. for 10 minutes to develop color the absorbance of each spot of the $PGE_2$ and the decomposition products thereof (correspond to $PGA_2$ group and $PGB_2$ group) was measured by a recording type densitometer (COSNO Densitometer Chromatoace D-109 type) to measure the area of the spot, and then the content of the $PGE_2$ in the sample was calculated from the area ratio. The remained percentage was shown by the ratio of the content of the $PGE_2$ group in the lyophilized samples obtained in Reference Examples 1–7 after storing them for 16 days at 45° C. to the content of the $PGE_2$ before storage. The results are shown in Table 5.

Table 5

| Derivative of Prostaglandin $E_2$ ($PGE_2$) | Stability when stored for 16 days at 45° C. | | |
|---|---|---|---|
| | Stablilizer | Amount per vial | Remained percentage |
| 16-Methyl-$PGE_2$ | Dextran 20* | 200 mg. | 95% |
| | Dextran 70** | 60 mg. | 95% |
| | Mannitol (cont.) | 56 mg. | 70% |
| | Untreated (cont.) | 0 | 60% |
| 3-Methyl-$PGE_2$ | Dextran 20 | 200 mg. | 100% |
| | Mannitol (cont.) | 56 mg. | 70% |
| | Untreated (cont.) | 0 | 60% |
| 3,16(R)-Dimethyl-$PGE_2$ | Dextran 20 | 200 mg. | 100% |
| | Mannitol (cont.) | 56 mg. | 70% |
| | Untreated (cont.) | 0 | 60% |
| 17-Oxo-15-epi-$PGE_2$ | Dextrin | 50 mg. | 100% |
| | Mannitol (cont.) | 56 mg. | 50% |
| | Untreated (cont.) | 0 | 0 |
| 16(R)-Hydroxy-$PGE_2$ | Glutathione Oxidized type glutathione | 20 mg. | 95% |
| | | 20 mg. | 95% |
| | Mannitol (cont.) | 56 mg. | 70% |
| | Untreated (cont.) | 0 | 60% |

*Mean molecular weight of 20,000
**Mean molecular weight of 70,000.

What is claimed is:

1. A stabilized oral prostaglandin composition comprising a therapeutically effective amount of a lyophilized composition which comprises (A) a prostaglandin E group compound and (B) an effective amount of at least one member selected from the group consisting of hydroxypropyl cellulose, hydroxyethyl cellulose, carboxymethyl cellulose, a lower alkyl cellulose, a dextran, and dextrin; and a pharmaceutically acceptable carrier for oral administration.

2. The stabilized oral prostaglandin composition as claimed in claim 1 wherein said prostaglandin E group compound is a member selected from the group consisting of 4(R),16(R)-dimethyl-prostaglandin $E_2$, 4(S),16(R)-dimethyl-prostaglandin $E_2$, 4(S),16(S)-dimethyl-prostaglandin $E_2$, 4(R),16(S)-dimethyl-prostaglandin $E_2$, 16(R,S)-methyl-20-methoxy-prostaglandin $E_2$, 16(S)-methyl-20-methoxy-prostaglandin $E_2$, and 16(R)-methyl-20-methoxy-prostaglandin $E_2$.

3. The stabilized oral prostaglandin composition as claimed in claim 2 wherein said prostaglandin E group compound is 16(S)-methyl-20-methoxy-prostaglandin $E_2$.

4. The stabilized oral prostaglandin composition as claimed in claim 1 wherein said lower alkylcellulose or ethylcellulose is methylcellulose.

5. The stabilized oral prostaglandin composition as claimed in claim 1 wherein said lyophilized composition comprises 16(S)-methyl-20-methoxy-prostaglandin $E_2$ and dextran.

6. The stabilized oral prostaglandin composition as claimed in claim 1 in which said lyophilized composition comprises from 5 to 250 mg of said member per 2–150γ of said prostaglandin E group compound.

7. The stabilized oral prostaglandin composition as claimed in claim 1 wherein said carrier is selected from the group consisting of mannitol, lactose, starch, magnesium stearate, talc, and mixtures thereof.

8. The stabilized oral prostaglandin composition as claimed in claim 1 wherein said dextran has a mean molecular weight of between 5,000 and 5,000,000.

9. A process of preparing a stable oral prostaglandin composition which comprises preparing an aqueous solution of a prostaglandin E group compound and an effective amount of at least one member selected from the group consisting of hydroxypropyl cellulose, hydroxyethyl cellulose, carboxymethyl cellulose, a lower alkyl cellulose, a dextran, and a dextrin; lyophilizing said solution to provide a lyophilized composition; and mixing a therapeutically effective amount of said lyophilized composition with a pharmaceutically acceptable carrier for oral administration.

10. The process as claimed in claim 9 wherein said prostaglandin E group is a member selected from the group consisting of 4(R),16(R)-dimethyl-prostaglandin $E_2$, 4(S),16(R)-dimethyl-prostaglandin $E_2$, 4(S),16(S)-dimethyl-prostaglandin $E_2$, 4(R),16(S)-dimethyl-prostaglandin $E_2$, 16(R,S)-methyl-20-methoxy-prostaglandin $E_2$, 16(S)-methyl-20-methoxy-prostaglandin $E_2$, and 16(R)-methyl-20-methoxy-prostaglandin $E_2$.

11. The process as claimed in claim 10 wherein said prostaglandin E group is 16(S)-methyl-20-methoxy-prostaglandin $E_2$.

12. The process as claimed in claim 9 wherein said lower alkylcellulose is methylcellulose or ethylcellulose.

13. The process as claimed in claim 9 wherein said lyophilized composition comprises 16(S)-methyl-20-methoxy-prostaglandin $E_2$ and dextran.

14. The process as claimed in claim 9 wherein said lyophilized composition comprises from 5 to 250 mg. of said member per 2–150γ of said prostaglandin E group compound.

15. The process as claimed in claim 9 wherein said carrier is selected from the group consisting of mannitol, lactose, starch, magnesium stearate, talc, and mixtures thereof.

16. The process as claimed in claim 9 wherein said dextran has a mean molecular weight of between 5,000 and 5,000,000.

17. A lyophilized pharmaceutical composition comprising as the active ingredient a therapeutically effective amount of a prostaglandin E group compound selected from the group consisting of 4(R),16(R)-dimethyl-prostaglandin $E_2$, 4(S),16(R)-dimethyl-prostaglandin $E_2$, 4(S),16(S)-dimethyl-prostaglandin $E_2$, 4(R),16(S)-dimethyl-prostaglandin $E_2$, 16(R,S)-methyl-20-methoxy-prostaglandin $E_2$, 16(S)-methyl-20-methoxy-prostaglandin $E_2$, and 16(R)-methyl-20-methoxy-prostaglandin $E_2$, and an effective amount of at least one member selected from the group consisting of hydroxypropyl cellulose, hydroxyethyl cellulose, carboxymethyl cellulose, a lower alkyl cellulose, a dextran, and dextrin.

18. The lyophilized pharmaceutical composition as claimed in claim 17, wherein said prostaglandin E group compound is 16(S)-methyl-20-methoxy-prostaglandin $E_2$.

* * * * *

UNITED STATES PATENT OFFICE
CERTIFICATE OF CORRECTION

Patent No. 4,113,882　　　　　　　　　　Dated September 12, 1978

Inventor(s) Kiyoshi Okazaki, et al

It is certified that error appears in the above-identified patent and that said Letters Patent are hereby corrected as shown below:

Column 4, line 57:　"prostagrandin" should be --prostaglandin--.

Column 10, line 20:　"or" should be --is--.

line 21:　"is" should be --or--.

Signed and Sealed this

Sixth Day of March 1979

[SEAL]

Attest:

RUTH C. MASON
*Attesting Officer*

DONALD W. BANNER
*Commissioner of Patents and Trademarks*